United States Patent [19]

Ferruti et al.

[11] Patent Number: 5,463,012
[45] Date of Patent: Oct. 31, 1995

[54] POLYCARBONATES AND THE USE THEREOF FOR THE PREPARATION OF BIOEROSIBLE MATRICES

[75] Inventors: Paolo Ferruti; Elisabetta Ranucci; Fabio Bignotti, all of Trezzano Sul Naviglio, Italy

[73] Assignee: Mediolanum Farmaceutici S.p.A., Milan, Italy

[21] Appl. No.: 157,153

[22] PCT Filed: Jun. 5, 1992

[86] PCT No.: PCT/EP92/01262

§ 371 Date: Dec. 10, 1993

§ 102(e) Date: Dec. 10, 1993

[87] PCT Pub. No.: WO92/22600

PCT Pub. Date: Dec. 23, 1992

[30] Foreign Application Priority Data

Jun. 14, 1991 [IT] Italy ................. MI91A1645

[51] Int. Cl.$^6$ .................................................. C08G 64/00
[52] U.S. Cl. .................................................. 528/196; 528/199
[58] Field of Search ..................... 528/196, 199

[56] References Cited

U.S. PATENT DOCUMENTS 4,105,641  8/1978  Buysch et al. ........................ 526/712
5,260,367  11/1993  Toda et al. ........................ 524/449

FOREIGN PATENT DOCUMENTS 42-9880  5/1967  Japan.
51-90323  8/1976  Japan.
59-80454  5/1984  Japan.
3-47750  2/1991  Japan.

*Primary Examiner*—James J. Seidleck
*Assistant Examiner*—Terressa M. Mosley
*Attorney, Agent, or Firm*—Bucknam and Archer

[57] ABSTRACT

Polycarbonates of formula (I) wherein a is an integer from 2 to 300; $R^1$ and $R^2$ are the same or different and are independently a polyester residue of formula (III) wherein x and y are integers from 1 to 50, $R^4$ and $R^5$, which are the same or different, are aliphatic straight or branched hydrocarbon chains having from 1 to 4 carbon atoms, $R^6$ is an aliphatic or alicyclic straight or branched chain having from 2 to 18 carbon atoms, or a polyoxyalkylene residue of formula (II), the two groups —$R^4$—COO and —$R^5$—COO being randomly distributed in the polyester residue, x and y being in any possible ratio from 0 to 100, are synthesized by reacting dihydroxy compounds with 1,1'-carbonyldiimidazole. They are useful for the preparation of bioerosible matrices for biologically active compounds.

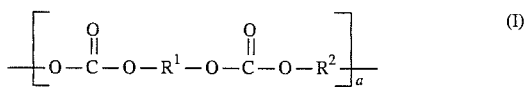

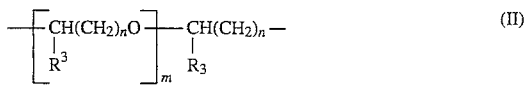

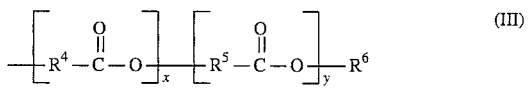

8 Claims, No Drawings

POLYCARBONATES AND THE USE THEREOF FOR THE PREPARATION OF BIOEROSIBLE MATRICES

This application is a 371 PCT/EP92/01262 filed Jun. 5, 1992.

The present invention relates to polycarbonates of formula (I)

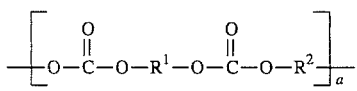

wherein
a is an integer from 2 to 300;
$R^1$ and $R^2$, which can be the same or different, are an aliphatic or alicyclic straight or branched chain having from 2 to 18 carbon atoms,
or $R^1$ and $R^2$ are a polyoxyalkylene residue of formula (II):

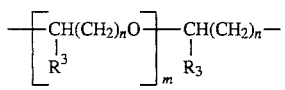

in which $R^3$ is hydrogen or methyl, n is an integer from 1 to 3 and m is an integer from 1 to 200,
or a polyester residue of formula (III)

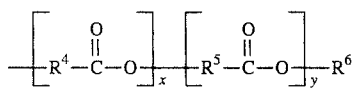

wherein x and y are integers from 1 to 50, $R^4$ and $R^5$, which can be the same or different, are aliphatic straight or branched hydrocarbon chains having from 1 to 4 carbon atoms, $R^6$ is an aliphatic or alicyclic straight or branched chain having from 2 to 18 carbon atoms, or a polyoxyalkylene residue of formula (II), being intended that the two groups —$R^4$—COO and —$R^5$—COO are randomly distributed in the polyester residue, x and y being in any possible ratio from 0 to 100.

When $R^1$ and/or $R^2$ are alkylene chains, these preferably have from 2 to 12 carbon atoms.

When $R^1$ and/or $R^2$ are polyoxyalkylene residues, these are preferably polyoxyethylene residues of formula (II) wherein $R^3$ is H, n is 1 and m is an integer from 2 to 100.

Polycarbonates in which $R^1$ and $R^2$ are hexylene, decylene, dodecylene, 1,4-cyclohexylene, 2,2-dimethyl-1,3-propylene, 2,5-dimethyl-2,5-hexylene or polyoxyethylene residues are preferred.

Particularly preferred are those polycarbonates in which $R^1$ and $R^2$ are selected from 1,4-cyclohexylene, 2,2-dimethyl-1,3-propylene, 2,5-dimethyl-2,5-hexylene or polyoxyethylene residues.

More particularly preferred are those polycarbonates in which $R^1$ and $R^2$ are polyester residues.

Most particularly preferred are those polycarbonates in which $R^1$ and $R^2$ are polyester residues, wherein $R^4$ and $R^5$ are methylene or methyl-methylene.

Groups $R^1$ and $R^2$ are preferably different from each other so as to give alternate co-polycarbonates, i.e. having regularly alternated monomeric units.

The invention further relates to a process for the preparation of compounds I and the use thereof for the preparation of pharmaceutical formulations slowly releasing the active principles.

Examples of pharmaceutical formulations in which the drug (active principle) is incorporated in a polymer matrix are well known in literature: See "Biodegradable Polymers as Drug Delivery Systems", ed. by M. Chasin and R. Langer, Marcel Dekker Inc., New York 1990; "Methods in Enzymology, Vol. 112, Drug and Enzyme Targeting, Part A", ed. by K. J. Widder and R. Green, Academic Press, Inc., Orlando, Fla. 1985; "Formes Pharmaceutiques Nouvelles", P. Buri, F. Puisieux, E. Doelker and J. P. Benoît, Technique et Documentation (Lavoisier), Paris 1985; "Biodegradable Polymers for controlled release of peptides and proteins", F. G. Hutchison and B. J. To. Furr, in Drug Carrier Systems, F. H. D. Roerdink and A. M. Kroom eds., John Wiley and Sons, Chichester, 1989; and "Controlled Release of Biologically Active Agents" by Richard Baker, John Wiley and Sons, New York 1987.

Aliphatic polycarbonates are known for example from DE 2546534, JP-62241920, JP-1009225, and they were proposed as plastifiers, intermediates for the preparation of polyurethanes or for special applications, such as the preparation of substrates for optical disks. The polycarbonates of the invention, having intrinsic viscosities in chloroform at 30° C. ranging from 0.05 dl/g to 2 dl/g, preferably from 0.077 to 0.32 dl/g, have biodegradability characteristics which make them useful for the preparation of bioerosible matrices.

Therefore, the invention also relates to pharmaceutical compositions providing a slow release of the active principles from bioerosible matrices comprising polycarbonates of formula (I).

Polymers of formula I are prepared by reacting diols of formula (IV) or (V)

wherein $R^1$ and $R^2$ are as defined above, with 2 moles of 1,1'-carbonyldiimidazole, to give diimidazolyl formates of formula (VI) or (VII)

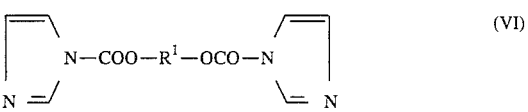

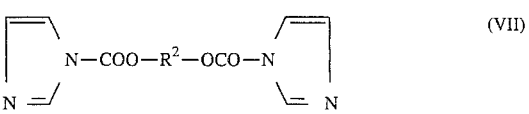

which are in their turn reacted with diols of formula (IV) or (V).

When $R^1$ and/or $R^2$ are polyester residues, then the compounds (IV) and (V) are synthetized under $N_2$ stream, at 200° C., starting from a mixture containing HO—$R^4$—COOH and HO—$R^5$—COOH in the desired ratio and 1–10% w/w of HO—$R^6$—OH and variable amounts of water.

The process is effected in aprotic solvents such as aliphatic or aromatic hydrocarbons, halogenated hydrocarbons, acetonitrile, dimethylsulfoxide, dimethylformamide, at a temperature from room temperature to the boiling temperature of the reaction mixture.

The following examples further illustrate the invention.

EXAMPLE 1

4.97 g of 1,1'-carbonyldiimidazole are added to an anhydrous solution of 3.05 g of polyethylene glycol 600 in 100 ml of "alcohol-free" chloroform. After 30 minutes the solution is stirred in the presence of 75 ml of water for 15 minutes; then it is extracted with 4×25 ml of water and dried over sodium sulfate. The organic phase is filtered, solvent is evaporated off to obtain 3.82 g of diimidazolyl formate, 2.1249 g of which are mixed with 1.00 ml of a 1,6-hexanediol anhydrous solution in admixture with 1:1 "alcohol-free" chloroform/dimethylsulfoxide having a concentration of 0.327 g/ml. After addition of 0.7538 g of imidazole and of a 1:1 chloroform/dimethylsulfoxide mixture to complete dissolution of the reagents, the solution is placed into a 60° C. bath for four days, after that it is diluted to 150 ml with chloroform, extracted with 5×30 ml of water, dried over anhydrous sodium sulfate and filtered. By evaporation of the solvent, 1.56 g of polycarbonate are obtained, which is liquid at 20° C. and has an intrinsic viscosity of 0.25 dl/g, measured in chloroform at 30° C. by means of Ubbelohde viscosimeter.

EXAMPLE 2

The procedure of example 1 is followed, using triethylene glycol instead of polyethylene glycol 600. The amounts are as follows:
1.21 g of triethylene glycol
6.34 g of 1,1'-carbonyldiimidazole.

2.51 g of diimidazolyl formate are obtained, 2.2111 g of which are reacted with 3.67 ml of a 1,6-hexanediol anhydrous solution of concentration 0.215 g/ml and 1.7656 g of imidazole, to obtain 1.90 g of polycarbonate, which is liquid at 20° C. and has an intrinsic viscosity of 0.16 dl/g in chloroform at 30° C.

EXAMPLE 3

The procedure of example 1 is followed, replacing polyethylene glycol 600 with triethylene glycol and of the 1,6-hexanediol with 1,10-decanediol. The amounts are as follows:
0.97 g of triethylene glycol
5.08 g of 1,1'-carbonyldiimidazole.

2.01 g of diimidazolyl formate are obtained, 1.7395 g of which are reacted with 3.37 ml of a 1,10-decanediol solution of concentration 0.278 g/ml and 1.3988 g of imidazole. 1.83 g of polycarbonate are obtained, having melting point of 26°–28° C. and viscosity of 0.17 dl/g in chloroform at 30° C.

EXAMPLE 4

The procedure of example 1 is followed, replacing polyethylene glycol 600 with triethylene glycol and 1,6-hexanediol with 1,12-dodecanediol. The amounts are as follows:
0.73 g of triethylene glycol
3.80 g of 1,1'-carbonyldiimidazole.

1.51 g of diimidazolyl formate are obtained, 1.2493 g of which are reacted with 2.41 ml of a 1,12-dodecanediol solution of concentration 0.312 g/ml and 0.9845 g of imidazole. 1.49 g of polycarbonate are obtained, having melting point of 34°–35° C. and intrinsic viscosity of 0.19 dl/g in chloroform at 30° C.

EXAMPLE 5

The procedure of example 1 is followed, using 2,2-dimethyl-1,3-propanediol instead of both polyethylene glycol 600 and 1,6-hexanediol. The amounts are as follows:
1.55 g of 2,2-dimethyl-1,3-propanediol
8.94 g of 1,1'-carbonyldiimidazole.

4.06 g of diimidazolyl formate are obtained, 3.4482 g of which are reacted with 4.63 ml of a 2,2-dimethyl-1,3-propanediol solution of concentration 0.259 g/ml and 2.8874 g of imidazole. 2.30 g of polycarbonate are obtained, having melting point of 70°–74° C. and intrinsic viscosity of 0.077 dl/g in chloroform at 30° C.

EXAMPLE 6

The procedure of example 1 is followed, replacing polyethylene glycol 600 with 2,2-dimethyl-1,3-propanediol and 1,6-hexanediol with 1,10-decanediol. The amounts are as follows:
1.62 g of 2,2-dimethyl-1,3-propanediol
9.37 g of 1,1'-carbonyldiimidazole.

4.25 g of diimidazolyl formate are obtained, 3.5386 g of which are reacted with 8.80 ml of a 1,10-decanediol solution of concentration 0.243 g/ml and 3.1437 g of imidazole. 3.86 g of polycarbonate are obtained, which is liquid at 20° C., and has an intrinsic viscosity of 0.21 dl/g in chloroform at 30° C.

EXAMPLE 7

The procedure of example 1 is followed, using 1,10-decanediol instead of both polyethylene glycol 600 and 1,6-hexanediol. The amounts are as follows:
1.30 g of 1,10-decanediol
4.64 g of 1,1'-carbonyldiimidazole.

2.43 g of diimidazolyl formate are obtained, 1.8584 g of which are reacted with 3.80 ml of a 1,10-decanediol solution of concentration 0.249 g/ml and 1.3768 g of imidazole. 2.06 g of polycarbonate are obtained, having melting point of 55°–57° C. and intrinsic viscosity of 0.19 dl/g in chloroform at 30° C.

EXAMPLE 8

The procedure of example 1 is followed, using 1,10-decanediol instead of polyethylene glycol 600 and 1,4-cyclohexanediol instead of 1,6-hexanediol. The amounts are as follows:
1.18 g of 1,10-decanediol
4.08 g of 1,1'-carbonyldiimidazole.

2.24 g of diimidazolyl formate are obtained, 1.7343 g of which are reacted with 2.45 ml of a 1,4-cyclohexanediol solution of concentration 0.229 g/ml and 1.4509 g of imidazole. 1.44 g of polycarbonate are obtained, having melting point of 91°–100° C. and intrinsic viscosity of 0.15 del/g in chloroform at 30° C.

EXAMPLE 9

8.39 g of 1,1'-carbonyldiimidazole are dissolved in an anhydrous solution prepared from 1.42 g of 1,4-cyclohexanediol, 20 ml of dimethylsulfoxide and 100 ml of "alcohol-free" chloroform. The procedure of example 1 is followed, to obtain 3.50 g of diimidazolyl formate, 2.7414 g of which are reacted with 6.82 ml of a 1,10 decanediol solution of concentration 0.243 g/ml and 6.8294 g of imidazole. 3.12 g of polycarbonate are obtained having melting point of 88°–93° C. and intrinsic viscosity of 0.13 dl/g in chloroform at 30° C.

EXAMPLE 10

The procedure of example 1 is followed, replacing 1,6-hexanediol with 1,10-decanediol. The amounts are as follows:
2.45 g of polyethylene glycol 600
2.48 g of 1,1'-carbonyldiimidazole.

2.78 g of diimidazolyl formate are obtained, 2.3646 g of which are reacted with 2.46 ml of a 1,10-decanediol solution of concentration 0.217 g/ml and 0.8538 g of imidazole. 2.19 g of polycarbonate are obtained, which is liquid at 20° C., having intrinsic viscosity of 0.28 dl/g in chloroform at 30° C.

EXAMPLE 11

The procedure of example 1 is followed, replacing 1,6-hexanediol with 2,2-dimethyl-1,3-propanediol. The amounts are as follows:
2.18 g of polyethylene glycol 600
2.23 g of 1,1'-carbonyldiimidazole.

2.47 g of diimidazolyl formate are obtained, 1.9386 g of which are reacted with 1.03 ml of a 2,2-dimethyl-1,3-propanediol solution of concentration 0.255 g/ml and 0.6935 g of imidazole. 1.74 g of polycarbonate are obtained, which is liquid at 20° C., having intrinsic viscosity of 0.21 dl/g in chloroform at 30° C.

EXAMPLE 12

The procedure of example 1 is followed, replacing 1,6-hexanediol with 1,4-cyclohexanediol. The amounts are as follows:
2.83 g of polyethylene glycol 600
3.16 g of 1,1'-carbonyldiimidazole.

3.24 g of diimidazolyl formate are obtained, 2.6828 g of which are reacted with 1.92 ml of a 1,4-cyclohexanediol solution of concentration 0.210 g/ml and 1.0459 g of imidazole. 2.39 g of polycarbonate are obtained, which is liquid at 20° C., having intrinsic viscosity of 0.26 dl/g in chloroform at 30° C.

EXAMPLE 13

The procedure of example 1 is followed, replacing polyethylene glycol 600 with 2,2-dimethyl-1,3-propanediol. The amounts are as follows:
0.78 g of 2,2-dimethyl-1,3-propanediol
4.54 g of 1,1'-carbonyldiimidazole.

2.07 g of diimidazolyl formate are obtained, 1.4731 g of which are reacted with 2.67 ml of a 1,6-hexanediol solution of concentration 0.223 g/ml and 1.4725 g of imidazole. 1.32 g of polycarbonate are obtained, which is liquid at 20° C., having intrinsic viscosity of 0.17 dl/g in chloroform at 30° C.

EXAMPLE 14

The procedure of example 1 is followed, replacing polyethylene glycol 600 with 2,2-dimethyl-1,3-propanediol and 1,6-hexanediol with 1,12-dodecanediol. The amounts are as follows:
0.95 g of 2,2-dimethyl-1,3-propanediol
5.40 g of 1,1'-carbonyldiimidazole.

2.58 g of diimidazolyl formate are obtained, 1.8902 g of which are reacted with 5.66 ml of a 1,12-dodecanediol solution of concentration 0.231 g/ml and 1.5611 g of imidazole. 1.92 g of polycarbonate are obtained, which is liquid at 20° C., having intrinsic viscosity of 0.19 dl/g in chloroform at 30° C.

EXAMPLE 15

The procedure of example 1 is followed, using 1,6-hexanediol instead of polyethylene glycol 600. The amounts are as follows:
0.87 g of 1,6-hexanediol
4.99 g of 1,1'-carbonyldiimidazole.

2.08 g of diimidazolyl formate are obtained, 1.4806 g of which are reacted with 2.80 ml of a 1,6-hexanediol solution of concentration 0.204 g/ml and 1.5163 g of imidazole. 1.31 g of polycarbonate are obtained, having melting point of 58°–60° C. and intrinsic viscosity of 0.18 dl/g in chloroform at 30° C.

EXAMPLE 16

The procedure of example 1 is followed, using 1,6-hexanediol instead of polyethylene glycol 600 and 1,10-decanediol instead of 1,6-hexanediol. The amounts are as follows:
1.04 g of 1,6-hexanediol
5.31 g of 1,1'-carbonyldiimidazole.

2.43 g of diimidazolyl formate are obtained, 1.7387 g of which are reacted with 4.10 ml of a 1,10-decanediol solution of concentration 0.241 g/ml and 1.7457 g of imidazole. 1.72 g of polycarbonate are obtained, having melting point of 40°–44° C. and intrinsic viscosity of 0.17 dl/g in chloroform at 30° C.

EXAMPLE 17

The procedure of example 1 is followed, using 1,10-decanediol instead of polyethylene glycol 600 and 1,12-dodecanediol instead of 1,6-hexanediol. The amounts are as follows:
1.04 g of 1,10-decanediol
3.56 g of 1,1'-carbonyldiimidazole.

2.05 g of diimidazolyl formate are obtained, 1.3943 g of which are reacted with 3.59 ml of a 1,12-dodecanediol solution of concentration 0.217 g/ml and 1.0176 g of imidazole. 1.41 g of polycarbonate are obtained, having melting point of 50°–52° C. and intrinsic viscosity of 0.21 dl/g in chloroform at 30° C.

EXAMPLE 18

The procedure of example 1 is followed, using polyethylene glycol 1000 instead of polyethylene glycol 600. The amounts are as follows:
4.10 g of polyethylene glycol 1000
2.96 g of 1,1'-carbonyldiimidazole.

3.84 g of diimidazolyl formate are obtained, 2.8818 g of which are reacted with 1.25 ml of a 1,6-hexanediol solution of concentration 0.248 g/ml and 0.6723 g of imidazole. 2.46 g of polycarbonate are obtained, which is liquid at 20° C., having viscosity of 0.32 dl/g in chloroform at 30° C.

EXAMPLE 19

The procedure of example 1 is followed, using 1,6-hexanediol instead of polyethylene glycol 600 and 1,4-cyclohexanediol instead of 1,6-hexanediol. The amounts are as follows:
1.04 g of 1,6-hexanediol
5.19 g of 1,1'-carbonyldiimidazole.

2.53 g of diimidazolyl formate are obtained, 1.6105 g of which are reacted with 2.83 ml of a 1,4-cyclohexanediol solution of concentration 0.216 g/ml and 1.7318 g of imidazole. 1.45 g of polycarbonate are obtained, having melting point of 110°–115° C. and intrinsic viscosity of 0.16 dl/g in chloroform at 30° C.

EXAMPLE 20

The procedure of example 1 is followed, using 2,2-dimethyl-1,3-propanediol instead of polyethylene glycol 600 and 1,4-cyclohexanediol instead of 1,6-hexanediol. The amounts are as follows:
0.80 g of 2,2-dimethyl-1,3-propanediol
5.06 g of 1,1'-carbonyldiimidazole.

2.01 g of diimidazolyl formate are obtained, 1.4315 g of which are reacted with 2.74 ml of a 1,4-cyclohexanediol solution of concentration 0.208 g/ml and 1.4337 g of imidazole. 1.23 g of polycarbonate are obtained, having melting point of 142°–148° C. and intrinsic viscosity of 0.10 dl/g in chloroform at 30° C.

EXAMPLE 21

The procedure of example 1 is followed, replacing polyethylene glycol 600 with triethylene glycol and 1,6-hexanediol with 1,4-cyclohexanediol. The amounts are as follows:
1.31 g of triethylene glycol
5.97 of 1,1'-carbonyldiimidazole.

2.72 g of diimidazolyl formate are obtained, 1.9292 g of which are reacted with 3.25 ml of a 1,4-cyclohexanediol solution of concentration 0.204 g/ml and 1.3529 g of imidazole. 1.65 g of polycarbonate are obtained, having melting point of 31°–34° C. and intrinsic viscosity of 0.14 dl/g in chloroform at 30° C.

EXAMPLE 22

The procedure of example 1 is followed, replacing polyethylene glycol 600 with 2,5-dimethyl-2,5-hexanediol and 1,6-hexanediol with 1,10-decanediol. The amounts are as follows:
1.19 g of 2,5-dimethyl-2,5-hexanediol
4.33 g of 1,1'-carbonyldiimidazole.

2.54 g of diimidazolyl formate are obtained, 1.9980 g of which are reacted with 4.49 ml of a 1,10-decanediol solution of concentration 0.232 g/ml and 1.6272 g of imidazole. 1.98 g of polycarbonate are obtained, which is liquid at 20° C., having viscosity of 0.23 dl/g in chloroform at 30° C.

EXAMPLE 23

The procedure of example 1 is followed, replacing polyethylene glycol 600 with 2,5-dimethyl-2,5-hexanediol and 1,6-hexanediol with triethylene glycol. The amounts are as follows:
1.12 g of 2,5-dimethyl-2,5-hexanediol
4.87 g of 1,1'-carbonyldiimidazole.

2.38 g of diimidazolyl formate are obtained, 1.7605 g of which are reacted with 3.63 ml of a triethylene glycol solution of concentration 0.218 g/ml and 1.3938 g of imidazole. 1.67 g of polycarbonate are obtained, which is liquid at 20° C., having viscosity of 0.16 dl/g in chloroform at 30° C.

EXAMPLE 24

40.00 g of a 90% DL-lactic acid aqueous solution are reacted with 11.26 g of glycolic acid and 2.58 g of 1,10-decanediol at a temperature of 200° C., with stirring, under nitrogen stream, for 24 hours. After that, the product is thoroughly dried and molecular weight is determined by osmometry (MW: 850). 2.52 g of the resulting oligomer are reacted with 1.11 g of 1,10-decanediol diimidazolyl formate (prepared as described in example 7) and 0.21 g of anhydrous imidazole in 5 ml of "alcohol-free" chloroform at a temperature of 60° C. for 10 days. Then the mixture is diluted in 70 ml of chloroform, washed with 5×20 ml of water, dried over anhydrous sodium sulfate and filtered. Solvent is evaporated off, to obtain 2.08 g of polycarbonate, which is solid at 25° C., having intrinsic viscosity of 0.32 dl/g, measured with a Ubbelhode viscosimeter in chloroform at 30° C.

EXAMPLE 25

The procedure of example 24 is followed, using in the first step, for the preparation of the oligomer, DL-lactic acid, glycolic acid and ethylene glycol, instead of 1,10-decanediol. The amounts are as follows:
32.08 g of 90% DL-lactic acid aqueous solution
2.31g of glycolic acid
3.35 g of ethylene glycol.

30.01 g of the oligomer are obtained, which is thoroughly dried. The molecular weight is determined by the osometric method (MW: 700). The subsequent polymerization steps is also carried out as described in example 24, using the new oligomer of MW 700 instead of the one of MW 850, and 1,10-decanediol diimidazolyl formate. The amounts are as follows:
2.32 g of oligomer
0.98 g of 1,10-decanediol diimidazolyl formate
0.22 g of anhydrous imidazole.

2.51 g of polycarbonate are obtained, having intrinsic viscosity of 0.30 dl/g in chloroform at 30° C.

EXAMPLE 26

The procedure of example 24 is followed, using DL-lactic and glycolic acid in the following amounts:
18.51 g of 90% DL-lactic acid aqueous solution
14.41 g of glycolic acid
2 g of 1,10-decanediol.

31.81 g of oligomer are obtained, of MW: 650, determined by osmometry. 4.51 g of said oligomer are reacted with 1.99 g of 1,10-decanediol diimidazolyl formate (prepared as described in example 7) and 0.38 g of anhydrous imidazole; the polymer is recovered as in example 24. 4.38 g of polycarbonate are obtained, having intrinsic viscosity of 0.42 dl/g in chloroform at 30° C.

EXAMPLE 27

3.01 g of the oligomer prepared in example 24 (mw: 850) are reacted with 1.11 g of 1,1'-carbonyldiimidazole in 6 ml of "alcohol-free" chloroform at a temperature of 60° C.; subsequently, 0.62 g of anhydrous 1,10-decanediol and 0.24 g of anhydrous imidazole are added to the reaction mixture, which is left to polymerize for 10 days at 60° C. Finally the product is purified, as described in example 24, to obtain 2.88 of polycarbonate, having intrinsic viscosity of 0.32 dl/g in chloroform at 30° C.

EXAMPLE 28

The procedure of example 27 is followed, using the oligomer prepared in example 24 (MW: 850). The amounts are as follows:
3.66 g of oligomer (MW: 850)
1.35 g of 1,1'-carbonyldiimidazole
5 ml of "alcohol-free" chloroform
0.75 g of 1,10-decanediol diimidazolyl formate
2.05 g of polycarbonate are obtained, having intrinsic viscosity of 0.45 dl/g in chloroform at 30° C.

EXAMPLE 29

3.00 g of the oligomer prepared in example 24 (mw: 850) are reacted with 1.08 g of 1,4-cyclohexanediol diimidazolyl formate (prepared in example 9) and 0.31 g of anhydrous imidazole at 60° C. for 10 days. The procedure of example 24 is followed, to obtain 9.00 g of polycarbonate, having intrinsic viscosity of 0.30 dl/g in chloroform at 30° C.

EXAMPLE 30

2.25 g of the oligomer prepared in example 25 (MW: 700) are reacted with 1.02 g of 1,1'-carbonyldiimidazole in 5 ml of "alcohol-free" chloroform for 30 min. Then 2.25 g of the same oligomer MW 700 and 0.22 g of anhydrous imidazole are added to the reaction mixture, which is left to react for 10 days at 60° C. Finally the product is purified, as described in example 24, to obtain 4.80 g of polycarbonate, having intrinsic viscosity of 0.34 dl/g in chloroform at 30° C.

EXAMPLE 31

3.00 g of the oligomer prepared in example 25 (MW: 700) are reacted with 1.45 g of triethylene glycol diimidazolyl formate in 5 ml of "alcohol-free" chloroform and 0.30 g of anhydrous imidazole. Diimidazolyl formate is prepared as described in example 2, with the following amounts:
1.30 g of triethylene glycol
6.45 g of 1,1'-carbonyldiimidazole.

The reaction mixture, which is left to react for 10 days at 60° C. Finally the polymer is recovered as described in example 24, to obtain 2.98 g of polymer, having intrinsic viscosity of 0.35 dl/g in chloroform at 30° C.

EXAMPLE 32

A mixture consisting of 45 mg of 1,12-dodecanediol-polycarbonate (see Example 17) and 5 mg of deslorelin (Des-Gly$^{10}$, D-Trp$^6$, Proethylamide$^9$), a LHRH agonist peptide, was melted at 70° C. to obtain a homogeneous mass, which, after cooling at 20° C., was milled and extruded from a piston equipped PTFE tube, under a 100 kg/cm$^2$ pressure and at 40° C. The so obtained cylindric formulation (2 mm diameter, 10 mm length) was sterilized with gamma rays and subsequently used for therapeutic subcutaneous grafts.

We claim:

1. A polycarbonate of formula (I)

$$\left[ -O-\overset{O}{\underset{\parallel}{C}}-O-R^1-O-\overset{O}{\underset{\parallel}{C}}-O-R^2- \right]_a \quad (I)$$

wherein a is an integer from 2 to 300; $R^1$ and $R^2$ are the same or different, and are independently a polyester residue of formula (III)

$$\left[ -R^4-\overset{O}{\underset{\parallel}{C}}-O- \right]_x \left[ -R^5-\overset{O}{\underset{\parallel}{C}}-O- \right]_y -R^6 \quad (III)$$

wherein x and y are integers from 0 to 50, $R^4$ and $R^5$, which are the same or different and are aliphatic straight or branched hydrocarbon chains having from 1 to 4 carbon atoms, $R^6$ is an aliphatic or alicyclic straight or branched chain having from 2 to 18 carbon atoms, or a polyoxyalkylene residue of formula (II)

$$\left[ -CH(CH_2)_nO- \atop \underset{R^3}{|} \right]_m -CH(CH_2)_n- \atop \underset{R_3}{|} \quad (II)$$

in which $R^3$ is hydrogen or methyl, n is an integer from 1 to 3 and m is an integer from 1 to 200, and said two groups —$R^4$—COO and —$R^5$—COO are randomly distributed in the polyester residue, x and y being in any ratio from 0 to 100.

2. The polycarbonate according to claim 1 wherein $R^1$ and $R^2$ are different from each other, thus forming alternate co-polycarbonates.

3. The polycarbonate according to claim 1 wherein $R^4$ and $R^5$ are methylene or methyl-methylene.

4. The polycarbonate according to claim 1 wherein said $R^4$—COO— and $R^5$—COO— are radicals obtained from lactic acid and glycolic acid.

5. The method of preparation of a polycarbonate of formula (I)

$$\left[ -O-\overset{O}{\underset{\parallel}{C}}-O-R^1-O-\overset{O}{\underset{\parallel}{C}}-O-R^2- \right]_a \quad (I)$$

wherein a is an integer from 2 to 300; $R^1$ and $R^2$ are the same or different, and are independently a polyester residue of formula (III)

$$\left[ -R^4-\overset{O}{\underset{\parallel}{C}}-O- \right]_x \left[ -R^5-\overset{O}{\underset{\parallel}{C}}-O- \right]_y -R^6 \quad (III)$$

wherein x and y are integers from 0 to 50, $R^4$ and $R^5$, which are the same or different and are aliphatic straight or branched hydrocarbon chains having from 1 to 4 carbon atoms, $R^6$ is an aliphatic or alicyclic straight or branched chain having from 2 to 18 carbon atoms, or a polyoxyalkylene residue of formula (II)

$$\left[ -CH(CH_2)_nO- \atop \underset{R^3}{|} \right]_m -CH(CH_2)_n- \atop \underset{R_3}{|} \quad (II)$$

to which $R^3$ is hydrogen or methyl, n is an integer from 1 to 3 and m is an integer from 1 to 200, and said two groups —$R^4$—COO and —$R^5$—COO are randomly distributed in the polyester residue, x and y being in any ratio from 0 to 100, which consists of the steps of 1) reacting 2 moles of 1,1'-carbonyldiimidazole with a diol of formula (IV) or (V)

HO—$R^1$—OH        (IV)

HO—$R^2$—OH        (V)

wherein $R^1$ and $R^2$ are as defined hereinabove, in an organic aprotic solvent which is a member selected from the group consisting of chloroform, acetonitrile, dimethylsulfoxide, and dimethylformamide, at a temperature from room temperature to the boiling temperature of the reaction mixture, whereby a diimidazole formate of formula VI or VII is obtained,

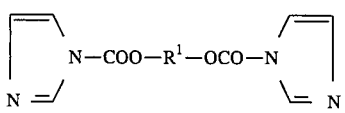 (VI)

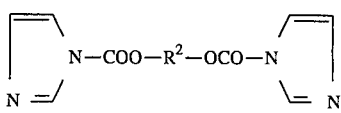 (VII)

wherein $R^1$ and $R^2$ are the same as hereinabove; and 2) then reacting said compound of formula VI or VII with a diol of formula (IV) or (V)

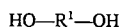 (IV)

or

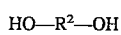 (V)

wherein $R^1$ and $R^2$ are the same as hereinabove, with imidazole in an organic aprotic solvent followed by extraction with water, drying said solvent and recovering said polycarbonate of formula (I) by evaporation of said organic aprotic solvent.

6. The method according to claim 5 wherein said diol in step 1) is a member selected from the group consisting of polyethylene glycol 600, triethylene glycol, 2,2-dimethyl-1,3-propanediol, 1,10-decanediol, 1,4-cyclohexanediol, polyethylene glycol 1000 and 2,5-dimethyl 2,5-hexanediol.

7. The method according to claim 5 wherein said diol in step 2) is a member selected from the group consisting of 1,6-hexanediol, 1,10-decanediol, 1,12-dodecanediol, 2,2-dimethyl-1,3-propanediol, 1,4-cyclohexanediol and triethylene glycol.

8. A pharmaceutical composition containing an active component and a bioerosible matrix comprising the polycarbonate of formula (I) according to claim 5.

* * * * *